United States Patent
Hahn et al.

(10) Patent No.: US 8,227,760 B2
(45) Date of Patent: Jul. 24, 2012

(54) HANDLING OF CONTAINERS WITH DIRT DETECTION

(75) Inventors: Wolfgang Hahn, Donaustauf (DE); Timo Pronold, Bad Abbach (DE); Johannes Boehm, Pentling (DE)

(73) Assignee: Krones AG, Neutraubling (DE)

( * ) Notice: Subject to any disclaimer, the term of this patent is extended or adjusted under 35 U.S.C. 154(b) by 147 days.

(21) Appl. No.: 12/869,689

(22) Filed: Aug. 26, 2010

(65) Prior Publication Data

US 2011/0049387 A1    Mar. 3, 2011

(30) Foreign Application Priority Data

Sep. 2, 2009  (DE) .......................... 10 2009 039 698

(51) Int. Cl.
*G01J 1/42* (2006.01)
(52) U.S. Cl. ..................................... 250/372; 250/338.1
(58) Field of Classification Search .................... 250/372
See application file for complete search history.

(56) References Cited

U.S. PATENT DOCUMENTS

| | | | | |
|---|---|---|---|---|
| 4,376,951 A | * | 3/1983 | Miyazawa | ..................... 348/127 |
| 4,551,627 A | * | 11/1985 | Reich | ........................ 250/339.12 |
| 4,858,768 A | * | 8/1989 | Plester | ............................ 209/3.1 |
| 5,067,616 A | * | 11/1991 | Plester et al. | ................... 209/3.1 |
| 5,486,693 A | | 1/1996 | Achter et al. | |
| 5,671,591 A | * | 9/1997 | Fleenor | ............................ 53/452 |
| 5,917,602 A | * | 6/1999 | Bonewitz et al. | ............. 356/614 |
| 2002/0154809 A1 | * | 10/2002 | Yamagishi et al. | ........... 382/142 |
| 2003/0214649 A1 | * | 11/2003 | Yagita | ........................ 356/239.5 |
| 2008/0232832 A1 | * | 9/2008 | Itoh et al. | ......................... 399/34 |

FOREIGN PATENT DOCUMENTS

| | | |
|---|---|---|
| CN | 2620274 Y | 6/2004 |
| DE | 42 00 971 A1 | 7/1993 |
| DE | 43 40 668 A1 | 8/1995 |
| DE | 10 2006 053 673 A1 | 5/2008 |
| EP | 0 362 679 A2 | 4/1990 |

* cited by examiner

*Primary Examiner* — David Porta
*Assistant Examiner* — Marcus Taningco
(74) *Attorney, Agent, or Firm* — Rissman, Hendricks & Oliverio, LLP

(57) ABSTRACT

A method of operating a device for the handling of containers, wherein the containers are conveyed at least locally through the device and are handled by the device in at least one pre-set manner, and wherein at least one flowable medium is used to operate the device. According to various aspects, pre-set areas of the device are irradiated by means of a radiation device in order to make at least one medium detectable in an area of the device in which the medium is present in a non-functional manner.

15 Claims, 1 Drawing Sheet

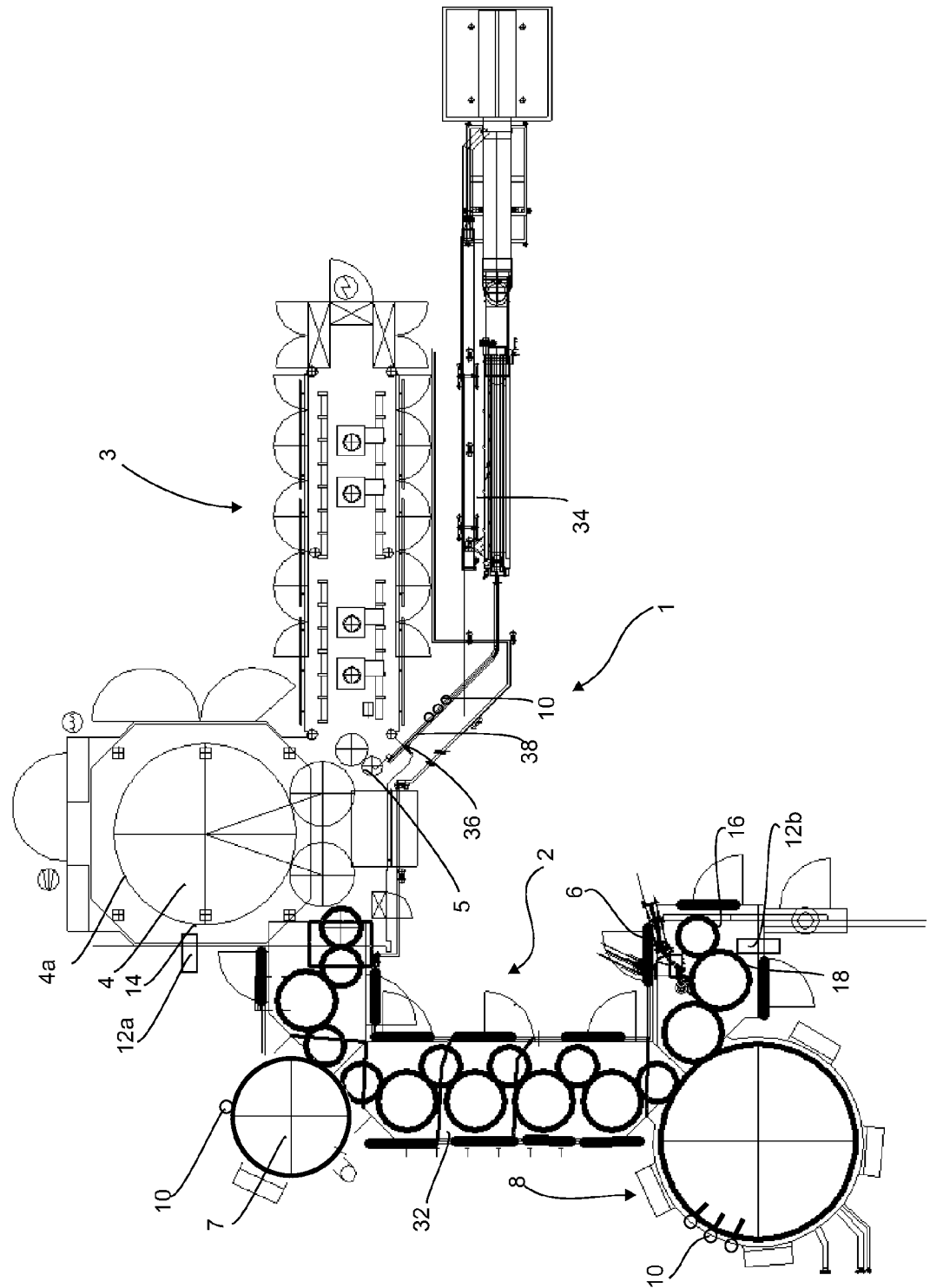

HANDLING OF CONTAINERS WITH DIRT DETECTION

CROSS-REFERENCE TO RELATED APPLICATION

This application claims the benefit of priority of German Patent Application No. 10 2009 039 698.5, filed Sep. 2, 2009, pursuant to 35 U.S.C. 119(a)-(d), the disclosure of which is incorporated herein by reference in its entirety as if fully set forth herein.

TECHNICAL FIELD

The present disclosure relates generally to a method and a device for operating a device for the handling of containers and, in particular, to the handling of containers with dirt detection.

BACKGROUND

Widely varying plants for the handling of containers are known from the prior art. In this way, so-called blow-moulding machines are known which usually expand plastics pre-forms by acting upon them with compressed air to form plastics containers. Furthermore, filling plants are also known which fill the containers, and also labelling stations which provide containers with labels. In this case plants of this type frequently require widely varying operating media such as for example adhesives in order to apply the labels to the containers, cooling or tempering liquids in order to heat blow moulds, or hydrogen peroxide gases in order to carry out sterilization processes.

In this case media of this type can lead to soiling or even contamination of plant components. Cleaning of the plants should therefore be carried out at regular intervals. In practice the problem also arises that the plants are cleaned only perfunctorily in part and, in this way, over time this can lead to dirt which in the worst case actually spoils the drink which is to be bottled.

A method of inspecting bottles or containers is known from DE 10 2006 053 673 A1, in which a pre-set quantity of an inspection or control liquid is introduced into the respective container and after being removed at least in part from the container this liquid is analysed for possible contamination. This method is thus used for the examination of the containers themselves which are to be filled in this case.

A method and a device for measuring contamination in reusable bottles or containers are known from DE 43 40 668 C2. In this case the containers themselves are examined for contamination whilst using a light beam passing through the bottle for example. A method and a device for detecting toxic substances in drinks bottles in filling lines are also known from DE 42 00 971 A1.

It may therefore be desirable to simplify the keeping clean of plants of this type for the handling of containers.

SUMMARY OF INVENTION

In an exemplary method according to the disclosure for operating a device for the handling of containers, the containers are conveyed at least locally through the device and are handled by the device in at least one pre-set manner. In this case, use is made of at least one flowable medium in order to operate the device.

According to the disclosure, pre-set areas of the device are irradiated by means of a radiation device in order to make at least one medium detectable in an area of the device in which the medium is present in a non-functional manner.

Handling of the containers can be understood as being the most widely varying types of handling, such as for example shaping pre-forms to form containers, filling the containers, labelling the containers, sterilizing the containers, rinsing the containers or even just simply conveying the containers.

The flowable medium can be both a gaseous medium and a liquid medium or even a viscous medium. A medium of which use is made during the operation of the device can be such a medium as is used for the handling of the containers, such as for example an adhesive in order to apply labels to the container, or even a sterilization substance in order to clean the wall of the container, or even for example lubricants in order to lubricate articulated links or even in order to operate cam rollers. The expression "make use of" can thus relate both to the containers and to the device itself, i.e. use can be made of the medium both during the handling of the containers themselves and during the operation of the device.

It is therefore proposed according to the disclosure that this medium should be detected in a region in which it is normally not present, for example a glue which has penetrated to other areas as a result of the operation of the machine or even a lubricant which has spread to places in which it does not benefit the proper functioning of the device or adversely affects or damages the operation of the device or even the device itself.

In the case of a gas there may be leakages for example which lead to the escape of the gas at undesired places. The radiation device acts upon areas of the device or even the medium itself with radiation, so that they react to it. In this way, cleaning the device is made easier for the machine operator, since he or she can recognize relatively quickly at which points dirt is present. In this way, it would be possible for example to irradiate in a purposeful manner those areas of the device at which, according to experience, penetrations of dirt can occur.

Furthermore, it is possible for leakages to be rapidly detected with the method according to the disclosure.

In some aspects, the medium may be a liquid or a viscous medium. In this case the medium can be for example a tempering medium of a blow mould to which for example additives can be added for detection purposes. In this way for example, it could be oil in the case of a heat-setting process or even water in the case of a standard process. These liquids can appear both through the base of the blow moulds and through blow-mould halves and in a plate in the region of the neck of the bottle.

Furthermore, leakages could arise in hose lines from a central distributor of the medium to the connections at the blow-moulding station as well as at the hoses from the blow-moulding station to the mould. Leakages of this type can arise in particular in the case of moved hoses which are moved by the opening and closing of the mould. In addition, hot substances such as for example hot oil at 160° C. can occur in part in the context of the blow-moulding shaping, so that safety risks can also be reduced by the present invention. Furthermore, so-called fixed control cams are generally used to move machine components, and these too require lubrication. Lubricating media of this type can likewise be transmitted to places at which they do not benefit the proper functioning of the device.

In various exemplary methods the medium comprises at least one substance which reacts in an (optically) perceptible manner to the radiation emitted by the radiation device. In this way, the medium could be for example a substance such as a glue which is visible under UV light or IR light for example.

If, therefore, the light of the radiation device strikes an area on which dirt could possibly be present, then this could be made detectable by a specified optical reaction such as for example illumination and in this way can be easily removed by the machine operator.

In some exemplary methods the medium is selected from a group of media which contains oils, fats, lubricants, glues, water, aqueous solutions, gases, for example hydrogen peroxide, and the like.

In various exemplary methods at least one surface of at least one device component is formed in such a way that it reacts in an (optically) perceptible manner to radiation. In this case the surface can fluoresce for example during radiation, but if dirt is present at specific areas it is likewise visible by a correspondingly diminished reaction of the surface in question.

According to various aspects of an exemplary method, at least one surface has a coating which is formed in such a way that it reacts in a perceptible manner to radiation. In this case the coating will react when it is struck directly by the radiation, but it will not react or will react less if dirt is present on this coating.

In some aspects of an exemplary method the radiation contains UV (ultraviolet) or IR (infrared) light. The radiation device can irradiate specific area of the device in a dot-like manner.

Furthermore, it would also be possible for the radiation source to be capable of being switched on specially in a cleaning or inspection operation. In addition, it would be possible for the radiation source to be switched on for example in the event of a fault or after a specified operating time. In this way, preventive cleaning is simplified to a considerable degree, since the operator need not polish the entire device but in fact only those areas with actual soiling from glue or medium.

The present disclosure further relates to a device for the handling of containers, with at least one handling unit in order to handle the containers in a pre-set manner, and at least one conveying device in order to convey the containers at least locally through the device, use being made of at least one flowable medium during the operation of the device. According to various aspects of the disclosure the device has a radiation device which irradiates pre-set areas of the device in order to make the flowable medium visible in those areas in which the flowable medium is present in a non-functional manner. In some aspects the device may have a supply device for supplying the containers and a removal device for removing the containers.

It is also proposed with respect to the device that a radiation device should be provided which is designed to detect dirt in non-functional areas of the device, so as to facilitate cleaning of the device.

In some aspects of the disclosure the device has a detection device which detects radiation activated by the radiation device. If for example dirt fluoresces or reacts in another way to the radiation, then a suitable detection device could detect this and emit a signal such as for example an alarm signal to the user.

According to various aspects the radiation device irradiates those areas of the machine which are situated—in the conveying direction of the containers—downstream with respect to those areas in which use is made of the medium in a functional manner.

In addition, it would be possible for the radiation device to irradiate those areas which are situated below those areas in which use is made of the medium in a functional manner. This is relevant for example when the media in question flow downwards under the action of gravity.

According to some aspects the radiation device is capable of being activated. In this way it can be activated by the user in an active manner or it can be activated automatically after specified time lapses or intervals.

In various aspects the device has at least one device for shaping plastics pre-forms to form containers and/or at least one device for labelling containers. For these types of device the present invention is particularly relevant since these devices use specified media in a purposeful manner in order to handle the bottle, such as for example glues or tempering media for tempering the blow mould.

Some further advantages and embodiments may become evident from the attached drawings.

BRIEF DESCRIPTION OF THE DRAWINGS

In the drawings:

FIG. 1 is a diagrammatic illustration of an exemplary plant according to various aspects of the disclosure.

DETAILED DESCRIPTION

FIG. 1 is a diagrammatic illustration of a device 1 according to the invention. This device 1 has a sorting device 34 for sorting pre-forms 10. The pre-forms are conveyed in the direction of a clock-timed wheel 5 by a first conveying unit 38 which in this case is designed in the form of a chute. The pre-forms not yet conveyed are separated upstream with respect to this clock-timed wheel. The reference number 36 designates a barring device by which the supply of the pre-forms can be barred.

After that, the pre-forms are conveyed separated through a heating device 3 with a further conveying device (not shown in detail) and are transferred from there to a blow-moulding device 4. This blow-moulding device has a carrier wheel 4a on which a plurality of blow-moulding station (not shown) are arranged in order to expand the plastics pre-forms to form containers.

This blow-moulding device is adjoined by a rinsing unit 7 for rinsing the containers. The containers are finally transferred to a filling device 8 by way of further conveying units 32. This filling device has a plurality of filling elements, in order to fill the containers with a liquid, such as a drink. This filling device is adjoined by a labelling station, in order to provide the containers with labels. In addition, devices which bring closures to the containers or which close the containers with the closures can also be provided here. The individual conveying units 32, 38 form a conveying device 2 as a whole.

The reference signs 12a and 12b designate radiation devices which irradiate specified device components, i.e. areas of the blow-moulding device 4 and the labelling device 6 with radiation, for example UV light or infrared light. If for example glue or even tempering media have penetrated to areas at which they are normally not present, then these areas can be irradiated by means of the radiation device 12a and 12b, in order to make such dirt visible. The reference numbers 14, 16, 18 designate generally diagrammatically areas which are irradiated by the radiation devices. It is advantageous for those areas of the device to be irradiated on which materials can stick or remain at least for a specific period of time.

In this case it is possible for the individual radiation devices 12a and 12b to be arranged stationary in each case in order to illuminate specified areas. It would also be possible, however, for the radiation devices 12a and 12b to be arranged so as to be movable, for example pivotable or displaceable, in order to scan specified areas of the device.

In addition, the radiation devices 12, 12b could be moved jointly along the conveying path on which the containers are also conveyed, in order to illuminate larger areas of the device in this way so as thus to be able to detect dirt more easily. The radiation device could also be designed in the form of a portable unit, which optionally also communicates in a cable-free manner to a central station, so that the user can take it with him or her in order to irradiate any desired areas of the device.

In addition, it would be possible for dirt to be detected in an automated manner by means of the radiation device, for example if a sensor device were provided which recognized the radiation or reflections emitted by the medium. In addition, if dirt were detected in particularly critical areas, the barring device 36 could interrupt the further supply of containers. The operator of the device could also be made aware of dirt in areas particularly critical to the machine by way of an alarm.

It will be apparent to those skilled in the art that various modifications and variations can be made to the blow moulding machine with cleaning system of the present disclosure without departing from the scope of the invention. Other embodiments of the invention will be apparent to those skilled in the art from consideration of the specification and practice of the invention disclosed herein. It is intended that the specification and examples be considered as exemplary only.

What is claimed is:

1. A method of operating a device for the handling of containers, the method comprising:
    conveying at least one container at least locally through the device;
    handling said at least one container with the device in at least one pre-set manner;
    using at least one flowable medium in order to operate the device; and
    irradiating pre-set areas of the device with a radiation device in order to make at least one of said at least one flowable medium detectable in one of said pre-set areas of the device in which said medium is present in a non-functional manner.

2. A method according to claim 1, wherein the medium is a liquid.

3. A method according to claim 1, wherein the medium comprises at least one substance which reacts in a perceptible manner to the radiation emitted by the radiation device.

4. A method according to claim 1, wherein the medium is selected from a group of media which contains oils, fats, lubricants, glues, water, aqueous solutions, and hydrogen peroxide.

5. A method according to claim 1, wherein at least one surface of at least one device component is formed in such a way that it reacts in a perceptible manner to the radiation.

6. A method according to claim 5, wherein at least one surface has a coating which is formed in such a way that it reacts in a perceptible manner to radiation.

7. A method according to claim 1, wherein the radiation contains UV light or IR light.

8. A method according to claim 1, wherein the medium is a viscous medium.

9. A device for handling containers, comprising:
    at least one handling unit structured and arranged to handle the containers in a pre-set manner; and
    at least one conveying device structured and arranged to convey the containers at least locally through the device,
    wherein use is made of at least one flowable medium during the operation of the device, and
    wherein the device includes a radiation device structured and arranged to irradiate pre-set areas of the device in order to make the flowable medium visible in one of said pre-set areas in which the flowable medium is present in a non-functional manner.

10. A device according to claim 9, further comprising a detection device for detecting radiation activated by the radiation device.

11. A device according to claim 10, wherein the radiation device irradiates those areas of the device which are situated, in the conveying direction of the containers, downstream with respect to those areas in which use is made of the medium in a functional manner.

12. A device according to claim 10, wherein the radiation device is capable of being activated.

13. A device according to claim 9, wherein the device further comprises at least one shaping device for shaping plastics pre-forms to form containers.

14. A device according to claim 13, wherein the device further comprises at least one labelling device for labelling containers.

15. A device according to claim 9, wherein the device further comprises at least one labelling device for labelling containers.

* * * * *